(12) United States Patent
Majdali

(10) Patent No.: US 11,865,262 B2
(45) Date of Patent: *Jan. 9, 2024

(54) OXYGEN THERAPY ADMINISTRATION METHODS AND RELATED APPARATUS

(71) Applicant: Jeff Majdali, Orange, CA (US)

(72) Inventor: Jeff Majdali, Orange, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 17/650,498

(22) Filed: Feb. 9, 2022

(65) Prior Publication Data

US 2022/0176058 A1  Jun. 9, 2022

Related U.S. Application Data

(63) Continuation of application No. 17/063,380, filed on Oct. 5, 2020, now Pat. No. 11,278,695.

(60) Provisional application No. 62/988,888, filed on Mar. 12, 2020.

(51) Int. Cl.
*A61M 16/06* (2006.01)
*A61M 16/00* (2006.01)

(52) U.S. Cl.
CPC ...... *A61M 16/0672* (2014.02); *A61M 16/024* (2017.08); *A61M 2016/0039* (2013.01); *A61M 2205/3334* (2013.01); *A61M 2205/502* (2013.01); *A61M 2205/583* (2013.01); *A61M 2230/65* (2013.01)

(58) Field of Classification Search
None
See application file for complete search history.

(56) References Cited

U.S. PATENT DOCUMENTS

| | | | |
|---|---|---|---|
| 5,535,738 A | 7/1996 | Estes | |
| 5,937,854 A * | 8/1999 | Stenzler | A61M 16/0051 128/204.23 |
| 6,105,575 A | 8/2000 | Estes | |
| 7,516,742 B2 | 4/2009 | Stenzler | |
| 7,942,824 B1 * | 5/2011 | Kayyali | A61M 16/0003 128/204.26 |
| 8,893,720 B2 | 11/2014 | Cohen | |
| 10,251,595 B2 | 4/2019 | Heruth | |
| 10,265,486 B2 | 4/2019 | Allum | |
| 10,271,739 B2 | 4/2019 | Freeman | |

(Continued)

OTHER PUBLICATIONS

ExSpiron Quick View, YouTube video, https://www.youtube.com/watch?app=desktop&v=jwpKW9q6or0, Mar. 10, 2016, 3 pages.

(Continued)

*Primary Examiner* — Joseph D. Boecker
*Assistant Examiner* — Thomas W Greig
(74) *Attorney, Agent, or Firm* — KOS IP Law LLP

(57) ABSTRACT

Methods and apparatus for administering oxygen therapy, and particularly high-flow oxygen therapy is disclosed herein. A respiratory monitoring system may non-invasively determine average peak inspiratory flow rate of a patient based on biofeedback response received from the patient. Medical air, oxygen, or a combination of both may be delivered to the patient at a flow rate equal to greater than the determined average peak inspiratory flow rate of the patient to meet or exceed inspiratory demand of the patient. Fraction of oxygen inspired by the patient may be determined based on the average peak inspiratory flow rate and may be adjusted through high-flow oxygen therapy meeting inspiratory demand to prevent entrainment of ambient air or through low-flow oxygen therapy by accounting for entrainment of ambient air based on the average peak inspiratory flow rate to address medical needs of the patient.

16 Claims, 8 Drawing Sheets

(56) References Cited

U.S. PATENT DOCUMENTS

| | | | |
|---|---|---|---|
| 10,702,166 B1* | 7/2020 | Freeman | A61B 5/0803 |
| 11,278,695 B2* | 3/2022 | Majdali | A61M 16/0672 |
| 2003/0062045 A1 | 4/2003 | Woodring | |
| 2008/0202520 A1* | 8/2008 | Mitton | A61M 16/024 |
| | | | 128/204.21 |
| 2009/0030335 A1* | 1/2009 | Kuchler | A61B 5/1135 |
| | | | 128/204.22 |
| 2009/0133699 A1 | 5/2009 | Nalagatla | |
| 2011/0041849 A1 | 2/2011 | Chen | |
| 2011/0197885 A1* | 8/2011 | Wondka | A61M 16/0465 |
| | | | 128/204.22 |
| 2016/0193438 A1 | 7/2016 | White | |
| 2017/0325695 A1 | 11/2017 | Freeman | |
| 2018/0085544 A1 | 3/2018 | Holyoake | |
| 2018/0098739 A1 | 4/2018 | Freeman | |
| 2018/0272081 A1* | 9/2018 | Porter | A61M 16/0816 |
| 2020/0329977 A1 | 10/2020 | Freeman | |

OTHER PUBLICATIONS

ExSpiron 1Xi, Respiratory Motion, URL: http://www.respiratorymotion.com/exspiron1xi, printed date Feb. 23, 2021, 3 pages.
International Search Report and Written Opinion for App. No. PCT/US2021/021582, dated Jun. 10, 2021, 6 pages.
International Preliminary Report on Patentability issued in App. No. PCT/US2021/021582, dated Sep. 6, 2022, 5 pages.

* cited by examiner

OXYGEN THERAPY ADMINISTRATION METHODS AND RELATED APPARATUS

CROSS-REFERENCE TO RELATED APPLICATIONS

This application is a continuation of U.S. patent application Ser. No. 17/063,380, filed on 2020 Oct. 5, which claims the benefits of U.S. Prov. Pat. App. Ser. No. 62/988,888, filed on 2020 Mar. 12, the entire contents of which are expressly incorporated herein by reference.

STATEMENT RE: FEDERALLY SPONSORED RESEARCH/DEVELOPMENT

Not applicable.

BACKGROUND

The various aspects and embodiments described herein relate to oxygen therapy in general, and high-flow oxygen therapy in particular, where a breathing gas, such as compressed air or oxygen, is delivered to a patient at a flow rate high enough to meet or exceed the patient's inspiratory demand.

Individuals, or patients, may require assistance with respiration, for example, to stabilize breathing and control blood gases. In such circumstances, high-flow oxygen therapy may be suitable for patients, where oxygen is delivered to the patient at a flow rate higher than that delivered in traditional oxygen therapy. However, flow rate of oxygen delivered in high-flow oxygen therapy may often not be high enough to meet or exceed inspiratory demand of patients due to lack of a simple, non-invasive, and accurate way to identify the correct flow rate of oxygen that meets or exceeds inspiratory demand. When flow rate of oxygen is not high enough to meet or exceed inspiratory demand, patients will entrain ambient air along with the delivered oxygen to make up for the insufficient oxygen flow, causing healthcare professionals administering high-flow oxygen therapy to be blind to the fraction of oxygen inspired by the patients, a vital metric of oxygenation.

Accordingly, there is a need in the art for an improved method and device to identify and deliver the correct flow rate of oxygen that meets or exceeds inspiratory demand of patients, and measure fraction of oxygen inspired by patients.

BRIEF SUMMARY

Methods and related apparatus for administering oxygen therapy, and particularly high-flow oxygen therapy is disclosed herein. A respiratory monitoring system may non-invasively receive biofeedback response from a patient's breathing in and out to determine the patient's average peak inspiratory flow rate. High-flow oxygen therapy may be administered by delivering breathing gas to the patient at a flow rate equal to or greater than the patient's average peak inspiratory flow rate to meet or exceed the patient's inspiratory demand. The breathing gas delivered to the patient may be adjusted in terms of its oxygen percentage. The oxygen percentage of the breathing gas may be adjusted to deliver the proper fraction of inspired oxygen to the patient. Fraction of oxygen inspired by the patient may be adjusted to address medical needs of the patient by controlling the oxygen concentration in the breathing gas outputted from a breathing gas source and setting the flow rate of the breathing gas to equal to or greater than the average peak inspiratory flow rate so that the patient does not entrain ambient air. Low blood oxygen saturation may be treated by increasing the fraction of oxygen inspired by the patient through high-flow delivery of breathing gas having an oxygen concentration greater than that of ambient air. In some instances, low-flow oxygen therapy, delivering breathing gas to the patient at a flow rate less than the patient's average peak inspiratory flow rate, may be administered to allow the patient to entrain ambient air to control the fraction of inspired oxygen.

In accordance with one embodiment of the present disclosure, there may be a method of administering high-flow oxygen therapy. The method may include providing a respiratory monitoring system. The respiratory monitoring system may have a computer and at least one biofeedback sensor. The computer may have a frame. At least one display and at least one processor may be coupled to the frame. The at least one biofeedback sensor may be configured to be attachable to a patient and electrically couplable to the computer. The biofeedback sensor may receive biofeedback response through the patient's torso. The respiratory monitoring system may either be configured to measure minute volume and respiratory rate or tidal volume of the patient based on the biofeedback response. The method may also include providing an air-oxygen blender. The air-oxygen blender may output air deliverable to the patient by a tube. The tube may be attachable to the patient and to the air-oxygen blender. The method may also include attaching the at least one biofeedback sensor to the computer of the respiratory monitoring system and to the patient. The method may also include reading the minute volume and the respiratory rate. Alternatively, the step may be reading the tidal volume outputted by the at least one display of the respiratory monitoring system in communication with the computer. The method may also include determining average peak inspiratory flow rate based on the minute volume and the respiratory rate. Alternatively, the step may be determining average peak inspiratory flow rate based on the tidal volume. The method may also include adjusting flow rate of air to be delivered to the patient from the air-oxygen blender to equal to or greater than the determined average peak inspiratory flow rate to meet or exceed the patient's inspiratory demand.

The respiratory monitoring system may be further configured to determine the average peak inspiratory flow rate and output the average peak inspiratory flow rate via the at least one display of the respiratory monitoring system. The step of determining average peak inspiratory flow rate may comprise reading the average peak inspiratory flow rate outputted by the at least one display of the respiratory monitoring system.

The method may also include attaching the tube to the patient and to the air-oxygen blender and delivering the air to the patient. The step of delivering the air to the patient may comprise delivering the air to the patient at the adjusted flow rate until blood oxygen saturation of the patient reaches a desired percentage. Alternatively, the step of delivering the air to the patient may comprise delivering the air to the patient at an unadjusted flow rate, and then at the adjusted flow rate. The method may also include changing oxygen concentration in the air delivered by the air-oxygen blender to achieve a desired fraction of oxygen inspired by the patient. The method may also include determining fraction of oxygen inspired by the patient based on the average peak inspiratory flow rate, an unadjusted flow rate of the air being delivered to the patient, concentration of oxygen in the air being delivered to the patient, and flow rate of ambient air inspired by the patient. The method may also include determining fraction of oxygen inspired by the patient based on the adjusted flow rate of the air being delivered to the patient and concentration of oxygen in the air being delivered to the patient. The method may also include decreasing the adjusted flow rate of air delivered to the patient from the-air oxygen blender as the fraction of oxygen inspired by the patient increases.

According to another aspect of the present disclosure, there may be a method of administering high-flow oxygen therapy. The method may include providing a respiratory monitoring system. The respiratory monitoring system may have a computer and at least one biofeedback sensor. The computer may have a frame. At least one display and at least one processor may be coupled to the frame. The at least one biofeedback sensor may be configured to be attachable to a patient and electrically couplable to the computer. The at least one biofeedback sensor may receive biofeedback response from the patient. The respiratory monitoring system may either be configured to measure minute volume and respiratory rate or tidal volume of the patient based on the biofeedback response. The method may also include providing a breathing gas source. The breathing gas source may output breathing gas deliverable to the patient by a tube. The tube may be attachable to the patient to the breathing gas source. The method may also include attaching the at least one biofeedback sensor to the computer of the respiratory monitoring system and to the patient. The method may also include attaching the tube to the patient and to the breathing gas source. The method may also include reading the minute volume and the respiratory rate. Alternatively, the step may be reading the tidal volume outputted by the at least one display of the respiratory monitoring system in communication with the computer. The method may also include determining average peak inspiratory flow rate based on the minute volume and the respiratory rate. Alternatively, the step may be determining average peak inspiratory flow rate based on the tidal volume. The method may also include adjusting flow rate of breathing gas to be delivered to the patient from the breathing gas source to equal to or greater than the determined average peak inspiratory flow rate. The method may also include adjusting oxygen concentration of the breathing gas based on a desired fraction of oxygen to be inspired by the patient. The method may also include delivering the breathing gas to the patient at the adjusted flow rate and at the adjusted concentration of oxygen to achieve the desired fraction of oxygen to be inspired by the patient.

The respiratory monitoring system may be further configured to determine the fraction of oxygen inspired by the patient and output the fraction of oxygen inspired by the patient via the at least one display of the respiratory monitoring system. The method may also include inputting the adjusted flow rate of the breathing gas being delivered to the patient into the respiratory monitoring system. The step of determining the fraction of oxygen inspired by the patient may comprise reading the fraction of oxygen inspired by the patient outputted by the at least one display of the respiratory monitoring system.

The oxygen concentration of the breathing gas may be equal to or greater than 21%. The breathing gas may be heated, humidified, and delivered to the patient through a nasal cannula.

The method may also include decreasing the adjusted flow rate as the fraction of oxygen inspired by the patient increases. Alternatively, the method may also include decreasing the concentration of oxygen of the breathing gas delivered to the patient as the fraction of oxygen inspired by the patient increases.

According to another aspect of the present disclosure, there may be a respiratory monitoring system used in administering oxygen therapy. The respiratory monitoring system may have a computer and at least one biofeedback sensor. The computer may have a frame. At least one display and at least one processor may be coupled to the frame. The at least one biofeedback sensor may be configured to be attachable to a patient and electrically couplable to the computer. The at least one biofeedback sensor may receive biofeedback response from the patient. The at least one processor may be configured by program instructions to determine minute volume and respiratory rate. Alternatively, the at least one processor may be configured by program instructions to determine tidal volume in real time. The at least one processor may be further configured by program instructions to determine average peak inspiratory flow rate in real time based on the minute volume and the respiratory rate. Alternatively, the at least one processor may be further configured by program instructions to determine average peak inspiratory flow rate in real time based on the tidal volume. The at least one display may be configured by program instructions to output the determined average peak inspiratory flow rate in real time.

The respiratory monitoring system may further include a sensor configured to detect flow rate of oxygen being delivered to the patient by an oxygen delivery system. The at least one processor may be further configured by program instructions to determine fraction of oxygen inspired by the patient in real time. The at least one display may be further configured to output the determined fraction of oxygen inspired by the patient in real time.

The at least one processor may be further configured by program instructions to determine fraction of oxygen inspired by the patient in real time based on the determined average peak inspiratory flow rate.

The at least one processor may be further configured by program instructions to communicate with a microcontroller of an automated oxygen delivery system to adjust flow rate of oxygen being delivered to the patient to equal to or greater than the determined average peak inspiratory flow rate to meet or exceed the patient's inspiratory demand.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
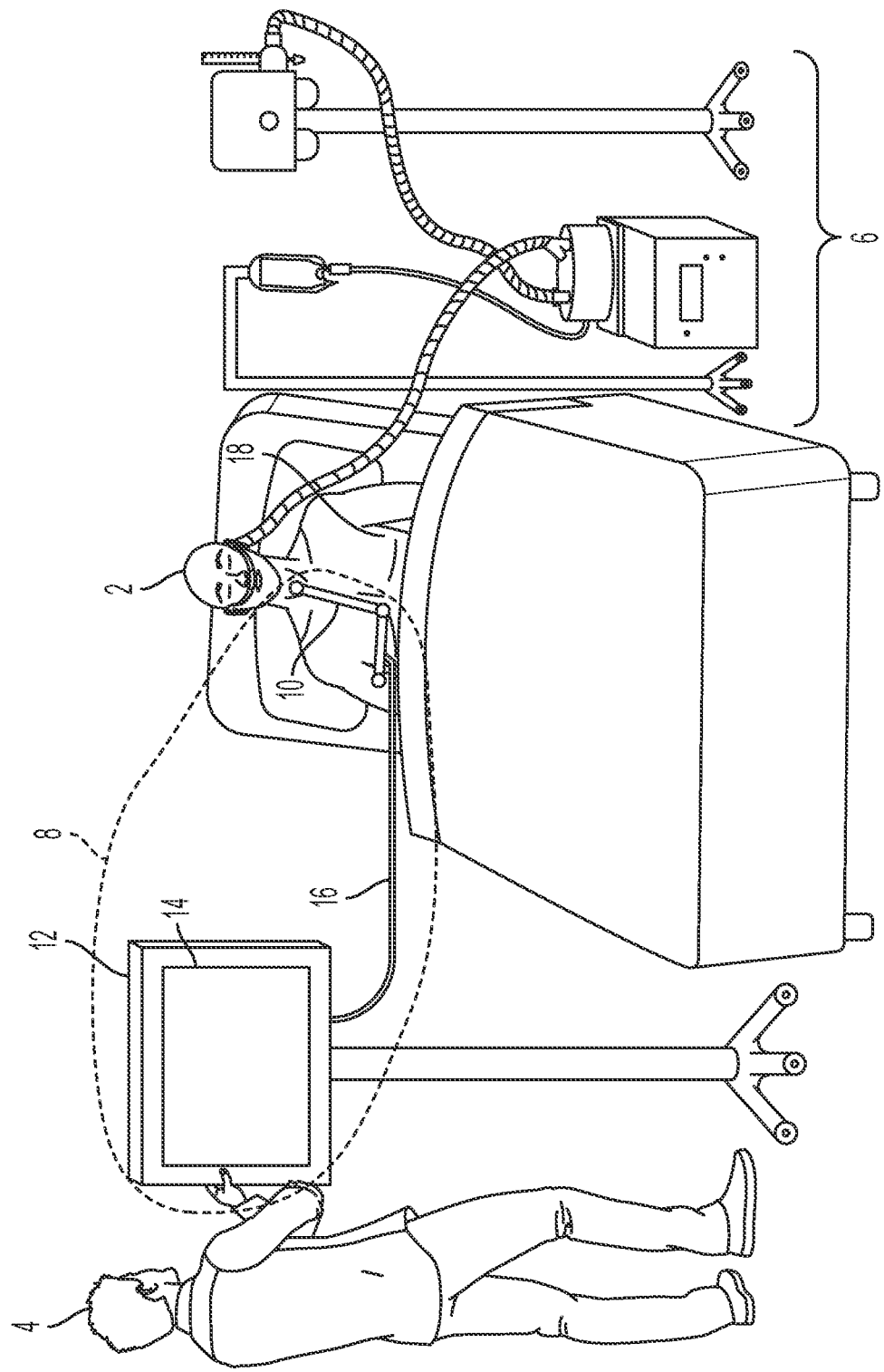
FIG. 1 is a perspective view of a respiratory therapist administering oxygen therapy to a patient.

Referring now to the drawings, apparatuses for administering oxygen therapy, and particularly high-flow oxygen therapy, a breathing gas source 6 and a respiratory monitoring system 8 is shown. (see FIG. 1) The respiratory monitoring system 8 may non-invasively receive biofeedback response from a patient 2 breathing in and out to determine average peak inspiratory flow rate of the patient 2. (see FIG. 1) High-flow oxygen therapy may be administered by delivering breathing gas to the patient 2 at a flow rate equal to or greater than the average peak inspiratory flow rate of the patient 2 to meet or exceed inspiratory demand of the patient 2. Also, the breathing gas is adjusted so the percent oxygen in the breathing gas is at the proper level for the patient 2. In this way, the fraction of inspired oxygen for that patient 2 is controlled. Alternatively, the fraction of oxygen inspired by the patient 2 may be controlled by accounting for air entrainment based on the difference of average peak inspiratory flow rate, the flow rate of breathing gas if the flow rate of the breathing gas is less than the average peak inspiratory flow rate, in other words low-flow and the percentage of oxygen of the breathing gas.

Referring now to FIG. 1, an individual, or the patient 2 receiving oxygen therapy is shown. Oxygen therapy may be administered by a second individual 4, who may be, for example, a respiratory therapist, a physician, or a caregiver. Oxygen therapy may be administered in a variety of settings, including hospitals, rehabilitation centers, ambulances, and home care. The patient 2 may be hooked up to the breathing gas source 6. The breathing gas source 6 may contain breathing gas having an oxygen concentration. In high-flow oxygen therapy, the breathing gas source 6 may deliver the breathing gas at a flow rate up to 60 L/min. In contrast, breathing gas sources used in traditional, or low-flow, oxygen therapy can generally deliver breathing gas at a flow rate up to 6 L/min.

The patient 2 may also be hooked up to the respiratory monitoring system 8. The respiratory monitoring system 8 may have a computer 12 that receives biofeedback response via a biofeedback sensor or sensors from the patient 2. The respiratory monitoring system may be operative to measure minute volume (MV), respiratory rate (RR), inspiratory time (I), expiratory time (E), tidal volume (TV) of the patient 2. Minute volume or MV is a volume of air inhaled by the patient in one minute. Respiratory rate or RR is the number of cycles of inhalation and exhalation taken by the patient in one minute. Inspiratory time is the time in seconds that the patient spends inhaling air as depicted by 20 in FIG. 2. Expiratory time is the time in seconds that the patient spends exhaling air as depicted by 22 in FIG. 2. Tidal volume or TV is the volume of air breathed in by the patient in one breath.

These values (MV, RR, I, E, TV) can be used to calculate other values and displayed on the display 14. The biofeedback sensors may be electrically coupled to the computer 12 to measure and display MV, RR, I, E, TV of the patient 2 on a display 14. In some embodiments, the biofeedback sensor or sensors may be electrode pad or pads 10 that deliver current to the patient 2 and receive biofeedback response, which may be bioimpedance signals generated by torso 18 movement due to breathing. In such embodiments, the electrode pads 10 may be electrically coupled to the computer 12 via a cable 16 placed on the torso 18 of the patient 2, to measure and display MV, RR, I, E, TV of the patient 2 on the display 14. The electrode pads 10 may have an adhesive back surface (not shown). In some embodiments, the electrode pads 10 may have the specifications of electrode pads sold as ExSpiron 1Xi PadSets sold by Respiratory Motion, Inc. In such embodiments, the electrode pads 10 may be positioned on the chest region of the patient 2 to create an L-shape as shown in FIG. 1. The electrode pads 10 may be centered on the chest and reach right below the neck and right under the pectoral muscle towards the armpit. In some embodiments, the electrode pads 10 may be generally positioned on the torso 18. In some embodiments, the respiratory monitoring system 8 may employ a respiratory inductance plethysmography device that measures changes in lung and/or abdominal volume during respiration. In such embodiments, the biofeedback sensors may be elastic belts (not shown) that have a shielded coiled wire sewn into them. The elastic belts may replace or be used in addition to the electrode pads 10. The elastic nature of the belts may allow for expansion and contraction of the torso 18 while the wire may carry current to create a magnetic field (not shown). When the patient 2 breathes, the torso 18 changes shape due to expansion and contraction, and thus changes the shape of the magnetic field. This induces an opposing current, which is measured as a change in frequency of the applied current. Then, the signals generated, which is the biofeedback response, may be received by the computer 12 of the respiratory monitoring system 8 to measure and display minute volume and respiratory rate, or display tidal volume of the patient 2 on the display 14.

Based on readings of the patient 2 from the respiratory monitoring system 8, the respiratory therapist 4 may determine average peak inspiratory flow rate of the patient 2. The readings may include minute volume and respiratory rate of the patient 2 or the tidal volume of the patient 2. Minute volume is the amount of breathing gas moved through the lungs of the patient 2 in one minute; respiratory rate is the number of breaths the patient 2 takes per minute; and tidal volume is the volume of breathing gas that is moved into and out of the lungs and airways in one breath (i.e., inhale once and exhale once). Peak inspiratory flow rate (PIFR) is the highest flow rate measured during an inspiratory period of a respiratory cycle of the patient 2. The desired determination to be made from the readings is average of the peak inspiratory flow rates observed in each inspiratory period within a given time period. If breathing gas supplied to the patient 2 is at a flow rate equal to or greater than the determined average peak inspiratory flow rate, inspiratory demand of the patient 2 will be met if flow rate is equal to the average peak inspiratory flow rate, or exceeded if flow rate is greater than the average peak inspiratory flow rate. The respiratory therapist 4 may adjust the flow rate outputted by the breathing gas source 6 to equal to or greater than the determined average peak inspiratory flow rate. By doing so, the respiratory therapist 4 may ensure that the inspiratory demand of the patient is met.

Figure 2:
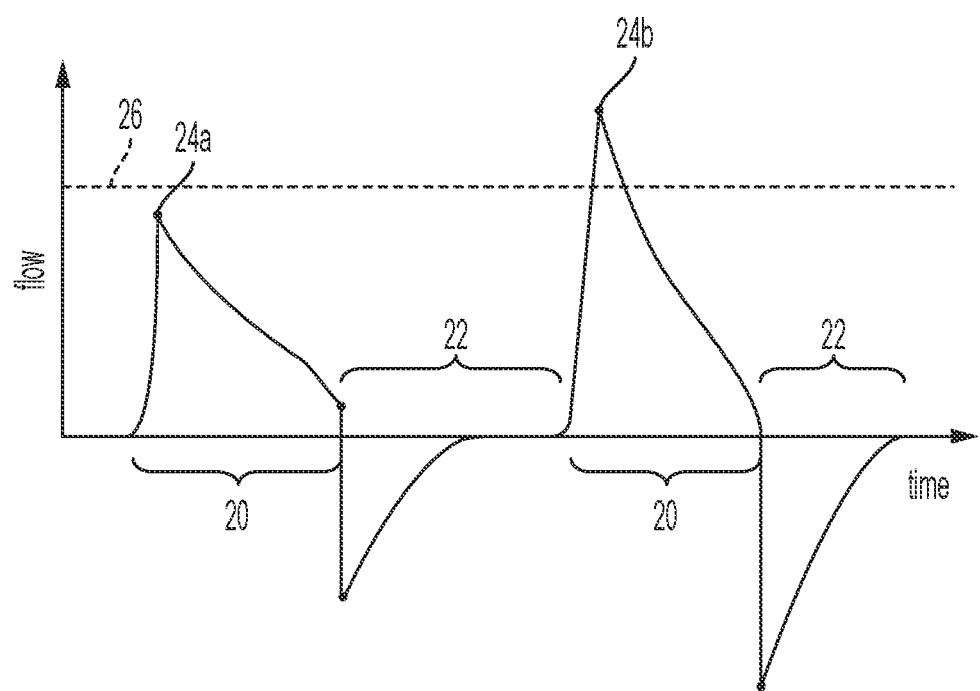
FIG. 2 is a flow rate graph of a respiratory cycle of the patient of FIG. 1.

Referring now to FIG. 2, flow versus time graph of a respiratory cycle is shown. Periods 20 on the graph represent inspiratory periods of the cycle where the patient 2 (see FIG. 1) is breathing in oxygen. Periods 22 on the graph represent expiratory periods of the cycle where the patient 2 is breathing out oxygen. Peaks 24a,b on the graph represent peak inspiratory flow of each inspiratory period 20. Inspiratory periods 20 may have durations indicating how slow or how quick the inhalation was for that period. For example, a shorter duration may indicate a quicker inhalation. Peak 24a may represent the peak inspiratory flow rate of an inspiratory period where the patient 2 inhales like they normally inhale. In an average adult, a normal peak inspiratory flow rate may be 30 L/min. Dashed lines 26 may indicate the average peak inspiratory flow rate of the patient 2. There may be an instance or instances where the patient 2 inhales so that peak inspiratory flow rate is higher than the average peak inspiratory flow rate in a given time period, for example, as indicated by peak 24b. A higher than average peak inspiratory flow rate such as peak 24b may occur if the patient 2 quickly draws in oxygen as opposed to a generally consistent pace when the patient 2 is idle. Hence, peak 24a may represent a peak inspiratory flow rate that may be closer to the average peak inspiratory flow rate than peak 24b. When breathing gas is supplied to the patient 2 at a flow rate equal to or greater than the determined average peak inspiratory flow rate, the patient 2 may instantaneously entrain ambient air to meet inspiratory demand at peak 24b. However, inspiratory demand will still be met overall for a time period by delivering breathing gas at the average peak inspiratory flow rate of that time period. Delivering breathing gas at a flow rate above the average peak inspiratory flow rate may further mitigate entrainment of ambient air at peaks such as 24b. However, adjusting the flow rate to only slightly above the average peak inspiratory flow rate, preferably between 0.5 to 6 L/min, more preferably between 0.5 to 3 L/min, is desirable to provide a comfortable delivery to the patient 2.

Referring back to FIG. 1, the respiratory therapist 4 may determine a fraction of oxygen inspired by the patient 2 based on the determined average peak inspiratory flow rate. Knowing the fraction of oxygen inspired by the patient 2 may help ensure the patient 2 is receiving the right amount of oxygen; neither too much nor too little. The respiratory therapist 4 may increase fraction of oxygen inspired by the patient 2 to a desired percentage by setting the flow rate to equal to or greater than the determined average peak inspiratory flow rate. When the flow rate is adjusted as such, the patient 2 may have no need to consistently entrain ambient air, which generally has an oxygen concentration of 21%. Hence, the fraction of oxygen inspired by the patient 2 may increase from 21% when breathing gas with higher oxygen concentration is delivered at the adjusted flow rate while the patient 2 has negligible or no need to entrain ambient air. If the fraction of oxygen inspired by the patient 2 reaches or exceeds a desired fraction of inspired oxygen, the flow rate of the breathing gas may be lowered. The lowered flow rate of the breathing gas may, stop, or counter the increase of fraction of inspired oxygen. In some embodiments, the flow rate of the breathing gas may be lowered to below the average peak inspiratory flow rate, or low-flow, to allow the patient 2 to entrain air. In such embodiments, the breathing gas may have an oxygen concentration up to 100%, and the difference of the average peak inspiratory flow rate and the flow rate of breathing gas may be accounted for flow rate of ambient air at 21% oxygen.

Increasing the fraction of oxygen inspired by the patient 2 may increase blood oxygen saturation of the patient. Generally, an average healthy adult may have a bloody oxygen saturation between 94% to 99%. However, if the patient 2 is suffering from low blood oxygen saturation, or hypoxemia, where the blood oxygen saturation is 90% or below, increasing the fraction of oxygen inspired by the patient 2 may increase blood oxygen saturation to between 94% to 99%. For example, bronchiectasis may be a respiratory illness where hypoxemia may be treated by high-flow oxygen therapy administered at or above the average peak inspiratory flow rate. In contrast, administering high-flow oxygen therapy without knowing the average peak inspiratory flow rate of the patient 2 would create the risk of not meeting or exceeding the inspiratory demand of the patient and cause the patient 2 to entrain ambient air with 21% oxygen concentration. Similarly, administering low-flow oxygen therapy without knowing the average peak inspiratory flow rate of the patient 2 would eliminate the possibility of accounting for ambient air entrainment in determining and regulating fraction of inspired oxygen. Hence, there would be a risk of blood oxygen saturation not rising to the desired range of between 94% to 99%. Determining average peak inspiratory flow rate and fraction of inspired oxygen of the patient 2 will be discussed in greater detail below for FIGS. 3A-5B.

Referring now to FIGS. 3A-5B, the computer 12 of the respiratory monitoring system 8 is shown. In some embodiments, the respiratory monitoring system 8 may have the specifications of the ExSpiron 1Xi respiratory monitoring system sold by Respiratory Motion, Inc. The respiratory monitoring system 8 (see FIG. 1) may have a processor or processors (not shown) that can be programmed to determine and display a variety of data related to the respiration of the patient 2 (see FIG. 1). The data may be received through the biofeedback sensors, which may be the electrode pads 10 or the elastic belts (not shown) placed on the torso 18 of the patient 2. (see FIG. 1) In some embodiments, the electrode pads 10 may receive an electrical signal from the computer 12 via the cable 16 and detect bioimpedance signals originating from the patient 2. (see FIG. 1) In some embodiments, the elastic belts may carry a current to the patient 2 and detect change in frequency of the current. The bioimpedance signals or signals generated by the change in current frequency may reflect the movement of the torso 18 of the patient 2 due to diaphragm expansion and contraction from breathing in and out. The bioimpedance signals or the signals generated by the change in current frequency may be converted to digital form, recorded, and displayed by the display 14 of the computer 12. In some embodiments, the computer 12 may communicate with a multi-parameter patient monitoring system (not shown) to further display the digitalized signals on a display of the multi-parameter patient monitoring system. The communication between the computer 12 and the multi-parameter patient monitoring system may require an adapter. By example and not limitation, the multi-parameter patient monitoring system may have the specifications of IntelliVue manufactured by Philips. Also, by example and not limitation, the adapter may have the specifications of IntelliVue MMX manufactured by Philips. The computer 12 may draw power from a wall outlet or may have an internal battery for portability.

Figure 3A:
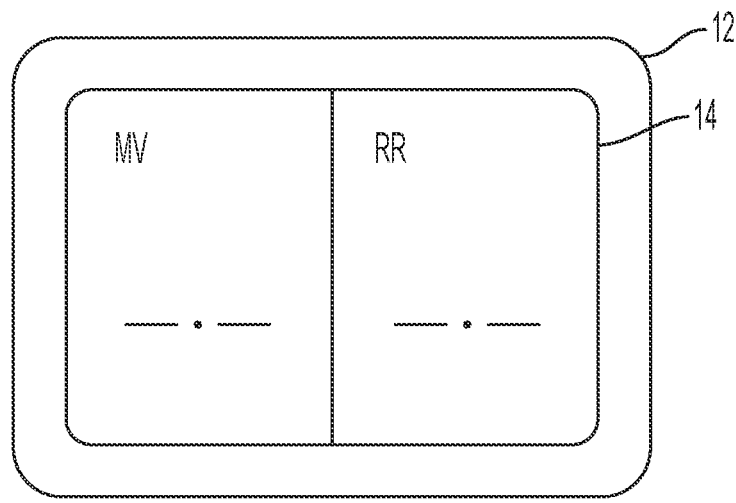
FIG. 3A is a front view of a first embodiment of a computer of a respiratory monitoring system shown in FIG. 1.

Referring now to FIG. 3A, the computer 12 may determine and display minute volume, or minute ventilation, and respiratory rate on the display 14. Minute volume is the amount of breathing gas moved through the lungs of the patient 2 (see FIG. 1) in a minute. It is a direct measurement of the respiratory status of the patient 2. In some embodiments, the displayed minute volume may have a unit of volume, such as L or mL. In some embodiments, the displayed minute volume may have a unit of volume over time, such as L/min, mL/min, L/s, or mL/s. Respiratory rate is the number of breaths the patient 2 takes per minute. In some embodiments, the displayed respiratory unit may have unit of breath over time, such as breaths/min, or bpm. In some embodiments, the displayed respiratory unit may have a unit of breaths. The respiratory therapist 4 (see FIG. 1) may determine the average peak inspiratory flow rate by plugging the displayed minute volume and the displayed respiratory rate into the following formula where average peak inspiratory flow rate is indicated by APIFR, minute volume is indicated by MV and respiratory rate is indicated by RR:

$$APIFR = MV \times \frac{60}{RR}.$$

The determined average peak inspiratory flow rate may have a unit of volume over time, such as L/min, L/s, mL/min, or mL/s. The flow rate outputted by the breathing gas source 6 (see FIG. 1) may then be adjusted to equal to or greater than the determined average peak inspiratory flow rate.

Figure 3B:
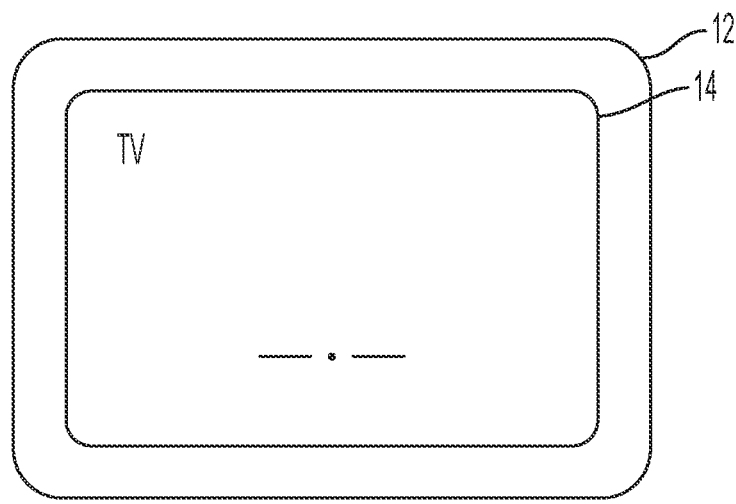
FIG. 3B is a front view of a second embodiment of the computer of the respiratory monitoring system shown in FIG. 1.

Referring now to FIG. 3B, the computer 12 may determine and display tidal volume on the display 14. Tidal volume is the volume of breathing gas that is moved into and out of the lungs and airways over a period of time. Tidal volume has the following relationship with minute volume and respiratory rate, where tidal volume is indicated by TV, minute volume is indicated by MV, and respiratory rate is indicated by RR: MV=TV×RR. In some embodiments, the displayed tidal volume may have a unit of volume, such as L or mL. In some embodiments, the displayed tidal volume may have a unit of volume over time, such as L/s, L/min, mL/min, or mL/s. The respiratory therapist 4 (see FIG. 1) may determine the average peak inspiratory flow rate by plugging the tidal volume into the following formula where average peak inspiratory flow rate is indicated by APIFR: APIFR=TV×60. The determined average peak inspiratory flow rate may have a unit of volume over time, such as L/min, L/s, mL/min, or mL/s. In some embodiments (not shown), the computer 12 may measure and the display 14 may display minute volume, tidal volume, and respiratory rate. In such embodiments, the respiratory therapist 4 may choose to use any of the above formulas to determine average peak inspiratory flow rate. The flow rate outputted by the breathing gas source 6 (see FIG. 1) may then be adjusted to be equal to or greater than the determined average peak inspiratory flow rate.

Figure 4A:
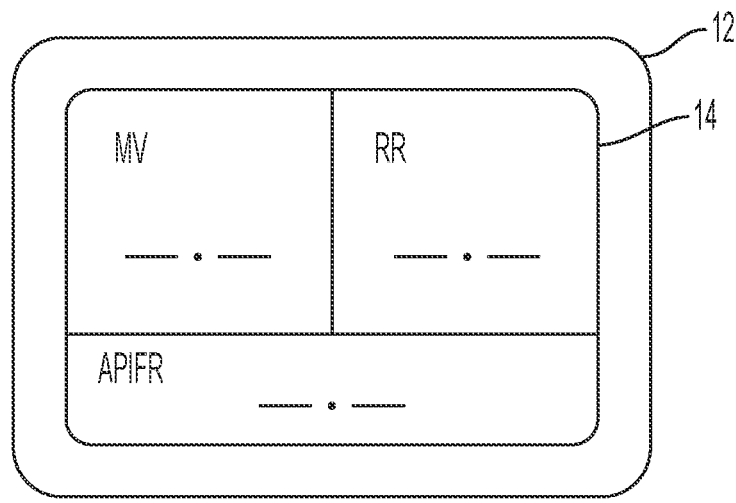
FIG. 4A is a front view of a third embodiment of the computer of the respiratory monitoring system shown in FIG. 1.
Figure 4B:
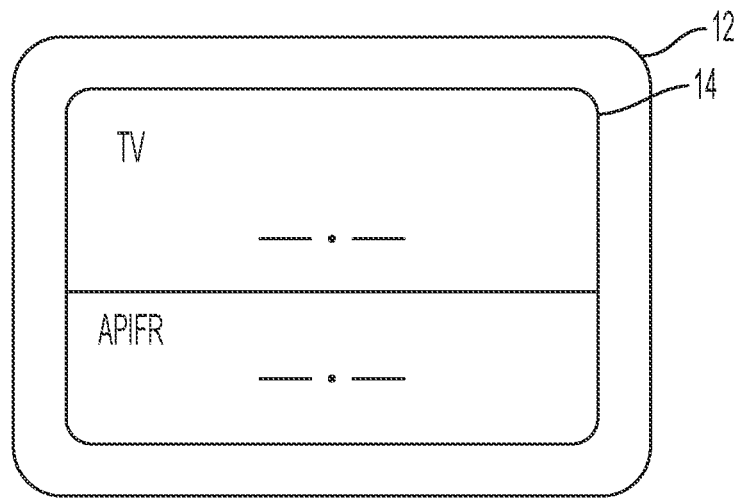
FIG. 4B is a front view of a fourth embodiment of the computer of the respiratory monitoring system shown in FIG. 1.
Figure 4C:
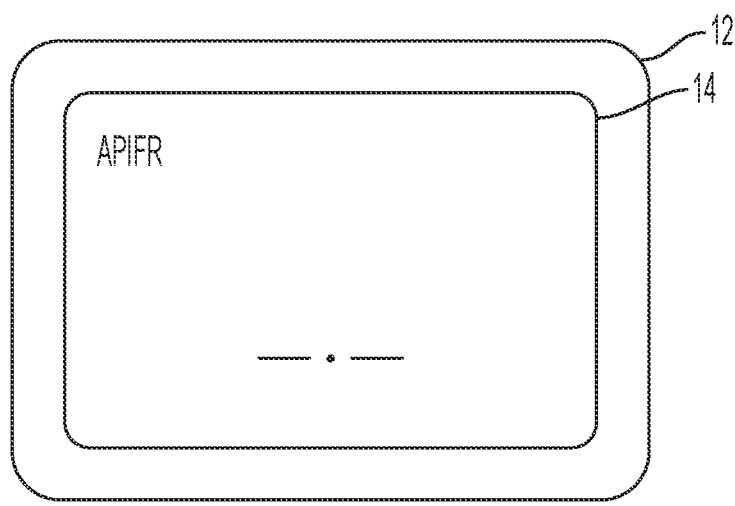
FIG. 4C is a front view of a fifth embodiment of the computer of the respiratory monitoring system shown in FIG. 1.

Referring now to FIGS. 4A-4B, the respiratory monitoring system 8 (see FIG. 1) may be configured to determine and output average peak inspiratory flow rate of the patient 2 (see FIG. 1). The average peak inspiratory flow rate may be displayed on the display 14. The displayed average peak inspiratory flow rate may have a unit of volume over time, such as L/min, L/s, mL/min, or mL/s. The processor of the computer 12 may compute the average peak inspiratory flow rate using the formula:

$$APIFR = MV \times \frac{60}{RR}$$

(or APIFR is equal to minute volume times 60 divided by respiratory rate). An alternate formula for APIFR may be APIFR is equal to minute volume times (inspiratory time plus expiratory time). In some embodiments, the processor of the computer 12 may additionally use the formula: MV=TV×RR. In some embodiments, minute volume and respiratory rate may additionally be displayed. (see FIG. 4A) In some embodiments, tidal volume may additionally be displayed. (see FIG. 4B) In some embodiments, only average peak inspiratory flow rate may be displayed. (see FIG. 4C) In some embodiments, minute volume, respiratory rate, and tidal volume may additionally be displayed. (not shown) The respiratory therapist 4 (see FIG. 1) may determine the average peak inspiratory flow rate by checking the display 14. The flow rate outputted by the breathing gas source 6 (see FIG. 1) may then be adjusted to be equal to or greater than the determined average peak inspiratory flow rate.

Figure 5A:
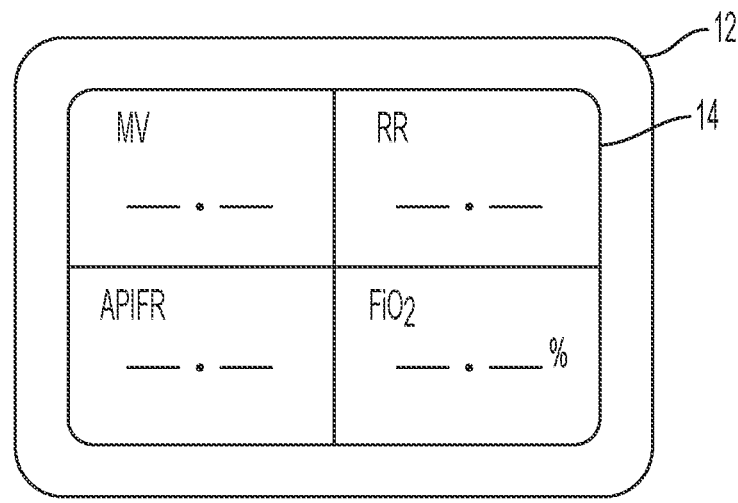
FIG. 5A is a front view of a sixth embodiment of the computer of the respiratory monitoring system shown in FIG. 1.
Figure 5B:
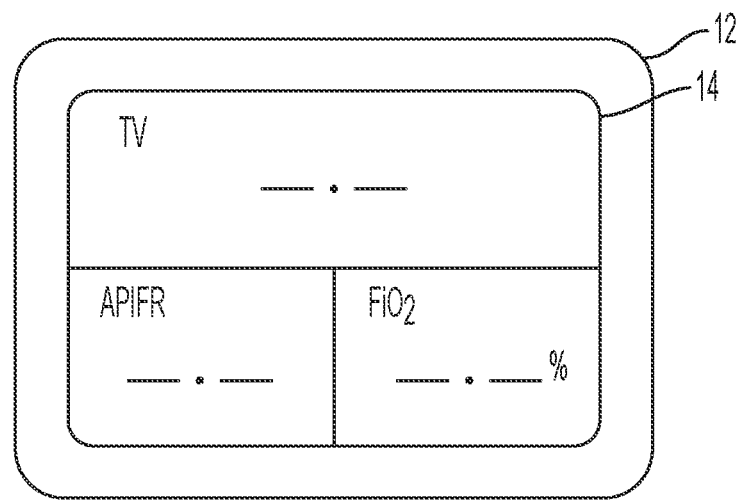
FIG. 5B is a front view of a seventh embodiment of the computer of the respiratory monitoring system shown in FIG. 1.

Referring now to FIGS. 5A-5B, respiratory monitoring system 8 (see FIG. 1) may be configured to determine fraction of inspired oxygen of the patient 2 (see FIG. 1). The determined fraction of inspired oxygen may be displayed on the display 14. The displayed fraction of inspired oxygen may be a percentage (%) or in decimals. In some embodiments, minute volume, respiratory rate, and average peak inspiratory flow rate may additionally be displayed. (see FIG. 5A) In some embodiments, tidal volume and average peak inspiratory flow rate may be additionally displayed. (see FIG. 5B) In some embodiments, minute volume, respiratory rate, tidal volume and average peak inspiratory flow rate may additionally be displayed. (not shown) In some embodiments, only average peak inspiratory flow rate may additionally be displayed. (not shown)

The processor of the computer 12 may compute the fraction of inspired oxygen based on average peak inspiratory flow rate, flow rate of breathing gas being delivered to the patient 2, and the concentration of oxygen in the breathing gas being delivered to the patient 2. In some embodiments, the flow rate of breathing gas being delivered may be manually inputted to the computer 12, for example, via a keypad, buttons, arrow keys, or a touch sensor of the display 14. (not shown) In some embodiments, the flow rate of breathing gas being delivered may be provided to the computer 12 through an electronic communication between the computer 12 and the breathing gas source 6. In some embodiments, the flow rate of breathing gas being delivered may be equal to the average peak inspiratory flow rate, either inputted manually or determined by the computer 12. In some embodiments, where flow rate of the breathing gas is equal to or greater than the average peak inspiratory flow rate, the processor may determine that fraction of inspired oxygen is equal to oxygen concentration of the breathing gas. In some embodiments, where breathing gas is being delivered to the patient 2 at a flow rate below the determined average peak inspiratory flow rate, the computer 12 may account for ambient air entrained by the patient 2. The processor of the computer 12 may compute the flow rate of ambient air being entrained by the patient 2 by calculating the difference between the average peak inspiratory flow rate and the flow rate of breathing gas being delivered. The processor of the computer 12 may then add the product of the flow rate of ambient air and the oxygen concentration of ambient air (21%) to the product of the flow rate of breathing gas being delivered and the oxygen concentration of the breathing gas, and divide the sum from the average peak inspiratory flow rate to find the fraction of oxygen inspired by the patient 2. In some embodiments, the respiratory therapist 4 (see FIG. 1) may determine the fraction of inspired oxygen by performing the calculations mentioned above in discussing FIGS. 5A-5B manually. For example, the respiratory therapist 4 may do the calculations by hand, refer to a chart or charts, or use a calculator.

Figure 6:
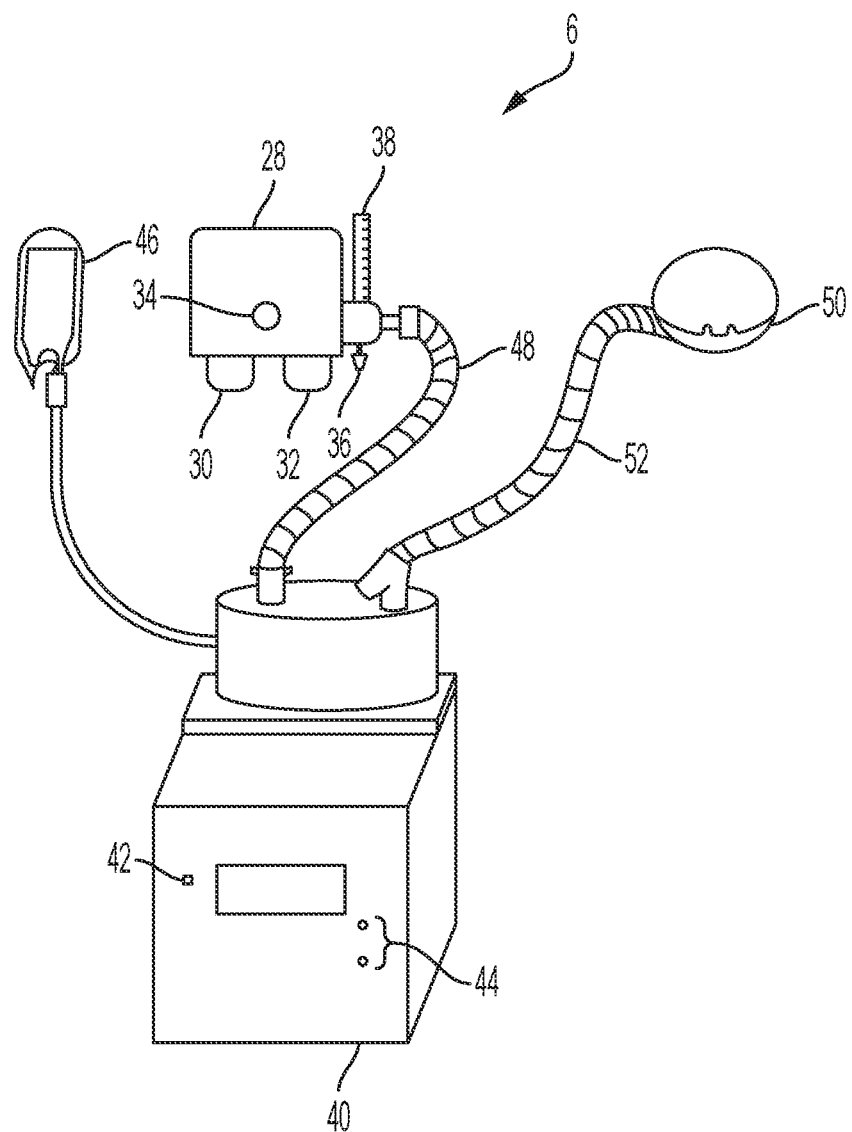
FIG. 6 is an enlarged perspective view of a breathing gas source shown in FIG. 1.

Referring now to FIG. 6, the breathing gas source 6 is shown. In some embodiments, the breathing gas source 6 may have the specifications of high-flow nasal cannula devices, Optiflow or AIRVO 2, manufactured by Fisher & Paykel. In some embodiments, the breathing gas source 6 may have the specifications of the high-flow nasal cannula device, VTU, manufactured by Vapotherm. The breathing gas source 6 may include the air-oxygen blender 28, also known as an oxygen proportioner. The air-oxygen blender 28 may receive a medical air tank 30 and an oxygen tank 32. The air-oxygen blender 28 may output gases from the medical air tank 30 and the oxygen tank 32 separately or as blended. In some embodiments, solely an oxygen tank 32 may be used in lieu of an air-oxygen blender. (not shown) Hence, the breathing gas delivered to the patient 2 (see FIG. 1) may be medical air, oxygen blended with medical air, or oxygen. The outputted breathing gas may have a concentration of 21% to 100% oxygen. Preferably, the oxygen concentration may be between 21% to 60%. Oxygen concentration greater than 60% delivered over an extended period of time, for instance more than 24 hours, may result in complications, for example damage to lungs or eyes. The concentration of oxygen outputted may be adjusted by turning a front control knob 34.

Flow rate of the breathing gas outputted by the air-oxygen tank may be adjusted by turning a control knob 36. When the control knob 36 is turned, a flowmeter 38 may show the adjustment by reading the flow rate of the outputted breathing gas. In some embodiments, the breathing gas source 6 may be in wired or wireless (e.g., Bluetooth, Wi-Fi, or infrared signal) electronic communication with the computer 12 of the respiratory monitoring system 8. In such embodiments, the breathing gas source 6 may relay breathing gas flow rate and or oxygen concentration data to the respiratory monitoring system 8. Also, in such embodiments, the respiratory monitoring system 8 may determine fraction of inspired oxygen based on the flow rate and the oxygen concentration data. Flow rate of the breathing gas during oxygen therapy may be between 1 L/min to 60 L/min. During high-flow oxygen therapy, flow rate of the breathing gas may be between 10 L/min to 60 L/min; preferably, between 30 L/min to 60 L/min. In some embodiments, the patient 2 (see FIG. 1) may receive breathing gas at a flow rate between 1 L/min to 10 L/min initially, and then receive high-flow therapy. In some embodiments, the patient 2 may receive breathing gas at a flow rate between 1 L/min to 60 L/min, and then the flow rate may be adjusted so that the patient 2 receives breathing gas at a flow rate equal to or greater than the determined average peak inspiratory flow rate. In some embodiments, the patient 2 may receive breathing gas at a flow rate lower than the average peak inspiratory flow rate, for example below 30 L/min.

The breathing gas source 6 may also have a humidifier and heater compartment 40. The humidifier and heater compartment 40 may humidify and warm up the breathing gas before delivery to the patient 2. The outputted breathing gas from the air-oxygen blender may flow to the humidifier and heater compartment through a tube 48. Humidified and heated breathing gas may provide comfort for the patient 2. The humidity and temperature may be displayed on a display 42 on the humidifier and heater compartment 40. The humidifier and heater compartment 40 may draw power from a wall outlet or may have an internal battery for portability. (not shown) The humidifier and heater compartment 40 may be powered on and off with a power button 42.

The humidification and heating settings may be adjusted using buttons 44. A humidifier reservoir 46 may be connected to the humidifier and heater compartment 40. The humidifier reservoir 46 may contain sterile water. The humidified and heated breathing gas may flow from the humidifier and heater compartment 40 to a nasal cannula 50 through a tube 52. In some embodiments, a Hudson mask, a Venturi mask, an anesthetic facemask, or another suitable device appreciated by one of ordinary skill in the art may replace the nasal cannula 50. (not shown) The nasal cannula 50 may be inserted to the nostrils of the patient 2 for breathing gas delivery. (see FIG. 1) The nasal cannula 50 may create a seal within the nostrils that may let negligible or no ambient air into the nostrils. If no ambient air is let into the nostrils, the patient 2 may entrain ambient air through the mouth if inspiratory demand of the patient 2 is not met nor exceeded. In some embodiments, the breathing gas source 6 may be a medical air tank or an oxygen tank having adjustable flow attached to a tube that leads to a nasal cannula or another suitable device appreciated by one of ordinary skill in the art may replace the nasal cannula. (not shown)

Figure 7:
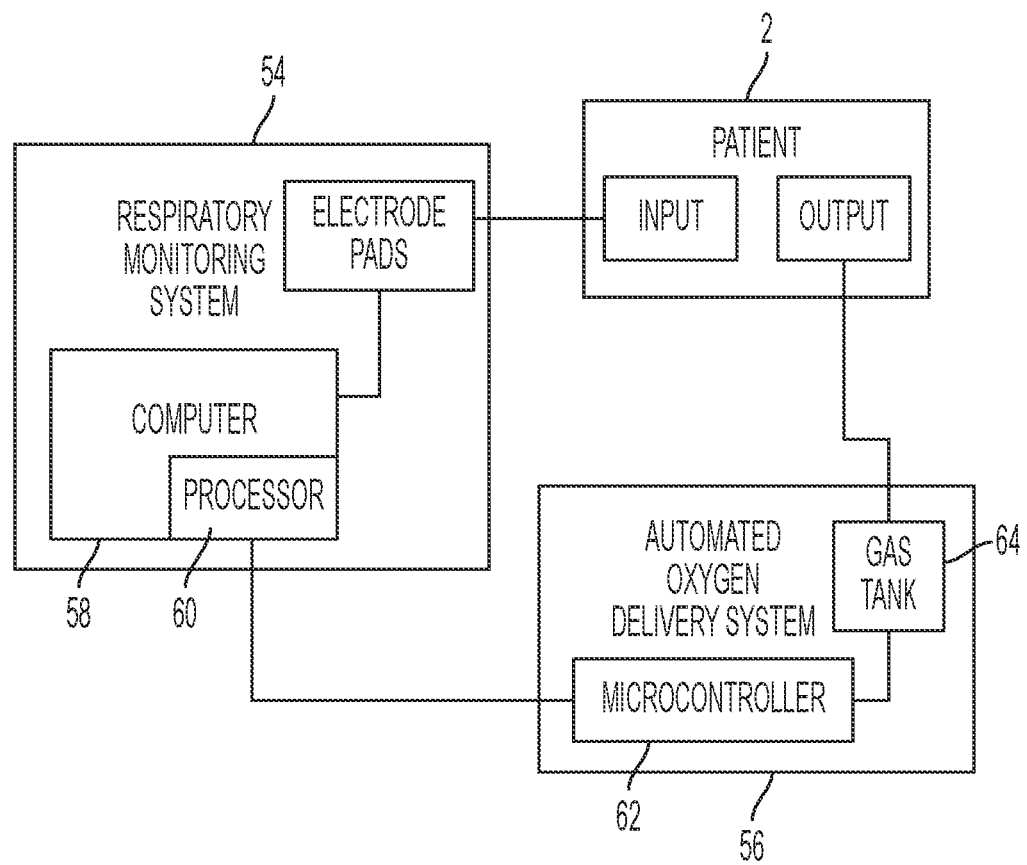
FIG. 7 is a diagram of a respiratory monitoring system, an automated oxygen delivery system, and the patient of FIG. 1 interacting with each other.

Referring now to FIG. 7, a diagram of a respiratory monitoring system 54 in electrical communication with the patient 2 and electronic communication with a breathing gas source or an automated oxygen delivery system 56 delivering breathing gas to the patient 2 is shown. The respiratory monitoring system 54 may have the specifications and operability of the respiratory monitoring system 8 shown in FIG. 1, except the additional capability to communicate, wired or wireless (e.g., Bluetooth, Wi-Fi, or infrared signal), with the automated oxygen delivery system 56. The automated oxygen delivery system 56 may have the specifications and operability of the breathing gas source 6 shown in FIG. 1, except the capability to automate breathing gas delivery based on input directly received from the respiratory monitoring system 56. The computer 58 may relay average peak inspiratory flow determined by processor(s) 60 to a microcontroller 62 of the automated oxygen delivery system 56. The microcontroller 62 may then communicate with a breathing gas tank 64 of the breathing gas source to adjust flow rate of breathing gas outputted by the breathing gas tank 64 to equal to or greater than the average peak inspiratory flow rate to meet the inspiratory demand of the patient 2. In some embodiments, when flow rate greater than the average peak inspiratory flow rate is desired, how much greater it can be may be preset. For example, a percentage of the average peak inspiratory flow rate or a specific rate increase may be added to the average peak inspiratory flow rate by the processor(s) 60 to determine the desired flow rate. In some embodiments, the oxygen concentration of the breathing gas tank 64 may be preset. In some embodiments, the oxygen concentration of the breathing gas tank 64 may be changed based on a desired fraction of inspired oxygen. In some embodiments, the computer 58 may communicate with the microcontroller 62 to relay a desired fraction of inspired oxygen to the microcontroller 62. The microcontroller 62 may then adjust the flow rate and/or the concentration of oxygen of the breathing gas to achieve or maintain the fraction of oxygen inspired by the patient 2.

As discussed herein, the inspiratory demand of the patient was described in relation to the average peak inspiratory flow rate. However, other ways of determining the inspiratory demands of the patent are contemplated. For example, the inspiratory demands can expressed in terms of the EstPIFR, last PIFR, greatest PIFR.

As discussed herein, the flow rate outputted by the breathing gas source 6 may be adjusted by the system or a clinician to be equal to or greater than the determined average peak inspiratory flow rate. However, it is also contemplated that the flow rate outputted by the breathing gas source 6 may be adjusted by the system or clinician to be equal to or greater than a last peak inspiratory flow rate, a greatest peak inspiratory flow rate over a period of time (e.g., past one minute or one minute) or an estimated peak inspiratory flow rate.

In relation to the last peak inspiratory flow rate, it is contemplated that the system would calculate the inspiratory flow rate based on the last inspiration of the patient and the system or clinician can adjust the flow rate outputted by the gas source 6 to be equal or greater than such inspiratory flow rate. In relation to the greatest peak inspiratory flow rate over a period of time, the system would record the peak inspiratory flow rate of each breath within a period of time, for example, one minute. The system can detect the highest PIFR and the system or the clinician can adjust the flow rate outputted by the gas source 6 to be equal to or greater than the highest PIFR detected by the system.

Additionally, it is also contemplated that the flow rate outputted by the breathing gas source 6 may be adjusted to be less than the last peak inspiratory flow rate, the greatest peak inspiratory flow rate over a period of time (e.g., past one minute or one minute) or an estimated peak inspiratory flow rate (EstPIFR).

The peak inspiratory flow rate (PIFR) may be calculated via the system (e.g., computer and the bioimpedance sensors or other bio feedback sensors) with the following formula: PIFR is equal to minute volume times (inspiratory time plus expiratory time). Alternatively, peak inspiratory flow rate may be calculated with the following formula: PIFR is equal to (tidal volume times respiratory rate) times (inspiratory time plus expiratory time).

The estimated peak inspiratory flow rate (EstPIFR) may be calculated with the following formula: EstPIFR=minute volume times "X" if respiratory rate is less than A or minute volume times "Y" if respiratory rate is greater than A. By way of example and not limitation, X may be 3 and Y may be 2 or one whole number less than X, and A may be 30. The system with the biofeedback sensors would measure the variables in the formulas provided herein and calculate/determine the PIFR.

As discussed herein the flow rate outputted by the breathing gas source 6 may be adjusted to be less than the various ways of determining the peak inspiratory flow rate (e.g., APIFR, EstPIFR, PIFR). One purpose of adjusting the flow rate to be lower than the various ways of determining the PIFR is to ween the patient off of supplemental oxygen.

In a clinical setting, it is beneficial to be able to know the fraction of inspired oxygen received by the patient. To do this, the inspiratory demands of the patient may be measured with the respiratory monitoring system 8 disclosed herein. The respiratory monitoring system 8 may measure peak inspiratory flow rate of the patient by measuring one or more of the MV, RR, I, E, TV of the patient. When the inspiratory demands (i.e., any one of the PIFRs discussed herein) of the patient is known, the fraction of inspired air received by the patient can be determined and the flow rate provided by the gas source to the patient can be set. For example, the flow rate provided by the gas source of the system can be adjusted to supply blended oxygen at a flow rate greater than the PIFR of the patient. If so, then the fraction of inspired oxygen is equal to the fraction of oxygen delivered to the patient by the gas source 6. The clinician can adjust the oxygen percentage at the gas source since in this scenario the oxygen percentage delivered by the gas source is equal to the fraction of inspired oxygen received by the patient. Based on the inspiratory demands of the patient, the clinician can set the system to deliver oxygen at a flow rate to achieve a target fraction of inspired oxygen for a particular patient.

If the flow rate provided by the gas source is lower than the PIFR of the patient, then the system can calculate the fraction of inspired oxygen and display the fraction of inspired oxygen received by the patient. The flow rate provided by the gas source may be set to be lower than the PIFR of the patient when weening the patient off of supplemental oxygen. When the flow rate of gas provided by the gas source is less than the inspiratory demand of the patient, then the fraction of inspired oxygen is a combination of oxygen provided by the gas source and oxygen due to entrainment of room air.

By way of example and not limitation, if the inspiratory demands of the patient is PIFR of 30 L/min of room air wherein room air has 21% oxygen, the average FiO2 the patient is receiving or breathing is calculated with the following formula: 30 L/min (PIFR) times 21% oxygen of room air is equal to 630 L/min-%, and 630 L/min-% divided by 30 L/min (PIFR) is equal to 21%. The FiO2 the patient is receiving is 21%. The reason is that 100% of the gas breathed in by the patient is room air which may have 21% oxygen.

Now, let's consider an example where the patient is receiving 20 L/min of oxygen via a high flow nasal cannula (HFNC) at a O2 (oxygen) percentage of 100%. The system measures the inspiratory demands of the patient and the inspiratory demands or PIFR of the patient is 30 L/min. Since the inspiratory demands of the patient is 10 L/min greater than the flow rate provided by the gas source, room air is entrained with the supplied oxygen at a rate of 10 L/min. The system determines the inspiratory demands of the patient, and the flow rate of gas with oxygen at a certain percentage is known. The FiO2 provided to the patient in this situation may be calculated as follows: (20 L/min times 100%) plus (10 L/min times 21%) is equal to 2210 L/min-%, and 2210 L/min-% divided by 30 L/min (PIFR) is equal to 73.7% FiO2. The system (e.g., computer) discussed herein may use the determined PIFR of the patient and the known oxygen percentage of room air to determine the FiO2 received by the patient.

If the patient has an inspiratory demand of 40 L/min and is still only receiving 20 L/min of supplied oxygen at 100% from the gas source, then the FiO2 provided to the patient is as follows: (20 L/min x 100%) plus (20 L/min x 21%)=2420 L/min-%, and 2420 L/min-% divided by 40 L/min (PIFR) is equal to 60.5% FiO2.

In the previous two examples, the nothing changed with the oxygen flow rate being delivered to the patient. Only the patient's PIFR or inspiratory demand changed and the system was capable of determining the FiO2 delivered to the patient due to the dilution of the supplied oxygen from the gas source due to entrainment of room air.

The various aspects discussed herein may be implemented when the patient is on a ventilator. Additionally, the various aspects discussed herein may be used while treating a patient who has trouble breathing. By way of example and not limitation, the gas discussed herein which is delivered to the patient has a certain percentage of oxygen.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of administering high-flow oxygen therapy, the method comprising the steps of:
providing a respiratory monitoring system, the respiratory monitoring system comprising:
a computer having:
a frame;
at least one display coupled to the frame;
at least one processor coupled to the frame; and
at least one bioimpedance sensor, the at least one bioimpedance sensor configured to be attachable to a torso of a patient and electrically couplable to the computer, and receive bioimpedance response from the patient;
wherein the respiratory monitoring system being configured to measure an inspiratory demand of the patient based on the bioimpedance response;
providing an air-oxygen blender, the air-oxygen blender outputting air deliverable to the patient by a tube attachable to the patient and to the air-oxygen blender;
attaching the at least one bioimpedance sensor to the computer of the respiratory monitoring system and to the patient wherein the respiratory monitoring system receives a signal from the at least one bioimpedance sensor to determine the inspiratory demand of the patient based on the signal from the at least one bioimpedance sensor and shows the inspiratory demand on the at least one display;
reading the inspiratory demand outputted by the at least one display of the respiratory monitoring system in communication with the computer;
determining a peak inspiratory flow rate based on the determined inspiratory demand;
adjusting flow rate of air to be delivered to the patient from the air-oxygen blender to equal to or greater than the determined peak inspiratory flow rate to meet or exceed the inspiratory demand of the patient; and
changing concentration of oxygen in the air delivered by the air-oxygen blender to increase or decrease oxygen inspired by the patient.

2. The method of claim 1 wherein the respiratory monitoring system is further configured to determine the peak inspiratory flow rate and output the peak inspiratory flow rate via the at least one display of the respiratory monitoring system, and wherein the step of determining peak inspiratory flow rate comprises reading the peak inspiratory flow rate outputted by the at least one display of the respiratory monitoring system.

3. The method of claim 1 further comprising the steps of attaching the tube to the patient and to the air-oxygen blender and delivering the air to the patient.

4. The method of claim 3 further comprising determining fraction of oxygen inspired by the patient based on the peak inspiratory flow rate, an unadjusted flow rate of the air being delivered to the patient, concentration of oxygen in the air being delivered to the patient, and flow rate of ambient air inspired by the patient.

5. The method of claim 3 further comprising determining fraction of oxygen inspired by the patient based on the adjusted flow rate of the air being delivered to the patient, and concentration of oxygen in the air being delivered to the patient.

6. A method of administering high-flow oxygen therapy, the method comprising the steps of:
providing a respiratory monitoring system, the respiratory monitoring system comprising:
a computer having:
a frame;
at least one display coupled to the frame;
at least one processor coupled to the frame; and
at least one bioimpedance sensor, the at least one bioimpedance sensor configured to be attachable to a torso of a patient and electrically couplable to the computer, and receive bioimpedance response from the patient;
wherein the respiratory monitoring system being configured to measure an inspiratory demand of the patient based on the bioimpedance response;
providing a breathing gas source, the breathing gas source outputting breathing gas deliverable to the patient by a tube attachable to the patient and to the breathing gas source;
attaching the at least one bioimpedance sensor to the computer of the respiratory monitoring system and to the patient;
attaching the tube to the patient and to the breathing gas source;
reading the measured inspiratory demand of the patient, the measured inspiratory demand of the patient being outputted to the at least one display of the respiratory monitoring system in communication with the computer;
determining a peak inspiratory demand based on the measured inspiratory demand;
adjusting flow rate of breathing gas to be delivered to the patient from the breathing gas source to equal to or greater than the determined peak inspiratory demand;
adjusting concentration of oxygen of the breathing gas; and
delivering the breathing gas to the patient at the adjusted flow rate and at the adjusted concentration of oxygen to achieve a target blood oxygen level of the patient.

7. The method of claim 6 wherein the respiratory monitoring system is further configured to determine the fraction of oxygen inspired by the patient and output the fraction of oxygen inspired by the patient via the at least one display of the respiratory monitoring system, further comprising inputting the adjusted flow rate of the breathing gas being delivered to the patient into the respiratory monitoring system.

8. The method of claim 6 wherein the oxygen concentration of the breathing gas is equal to or greater than 21%.

9. The method of claim 6 wherein the breathing gas is heated, humidified, and delivered to the patient through a nasal cannula.

10. A respiratory monitoring system used in administering oxygen therapy, comprising:
a computer having:
a frame;
at least one display coupled to the frame;
at least one processor coupled to the frame;
at least one bioimpedance sensor, the at least one bioimpedance sensor configured to be attachable to a torso of a patient and electrically couplable to the computer, and receive bioimpedance response from the patient;
wherein the at least one processor is configured by program instructions to:
determine an inspiratory demand of the patient in real time; and determine a peak inspiratory demand in real time based on the determined inspiratory demand; and begin flow of gas to a patient after the instructions to determine the inspiratory demand of the patient are carried out by the processor;

wherein the at least one display is configured by program instructions to output the determined peak inspiratory demand in real time.

11. The respiratory monitoring system of claim 10 further comprising a sensor configured to detect flow rate of oxygen being delivered to the patient by an oxygen delivery system.

12. The respiratory monitoring system of claim 11 wherein the at least one processor is further configured by program instructions to determine fraction of oxygen inspired by the patient in real time.

13. The respiratory monitoring system of claim 12 wherein the at least one display is further configured to output the determined fraction of oxygen inspired by the patient in real time.

14. The respiratory monitoring system of claim 10 wherein the at least one processor is further configured by program instructions to determine fraction of oxygen inspired by the patient in real time based on the determined peak inspiratory flow rate.

15. The respiratory monitoring system of claim 10 wherein the at least one processor is further configured by program instructions to communicate with a microcontroller of an automated oxygen delivery system to adjust flow rate of oxygen being delivered to the patient to equal to or greater than the determined peak inspiratory demand to meet or exceed the inspiratory demand of the patient.

16. The respiratory monitoring system of claim 10 wherein the peak inspiratory demand is an estimated peak inspiratory flow rate, last peak inspiratory flow rate, or greatest peak inspiratory flow rate.

* * * * *